United States Patent [19]

Daumas et al.

[11] 3,969,424

[45] July 13, 1976

[54] PROCESS FOR OXYCHLORINATION OF HYDROCARBONS

[75] Inventors: Jean-Claude Daumas, Marly-le-Roi; Madeleine Le Page, Paris, both of France

[73] Assignee: Rhone-Progil, Paris, France

[22] Filed: Sept. 3, 1974

[21] Appl. No.: 502,804

Related U.S. Application Data

[62] Division of Ser. No. 226,929, Feb. 16, 1972, Pat. No. 3,849,338.

[52] U.S. Cl. ............................ 260/662 A; 252/441
[51] Int. Cl.² .................... C07C 17/10; C07C 17/15
[58] Field of Search ................................ 260/662 A

[56] References Cited
UNITED STATES PATENTS

| | | | |
|---|---|---|---|
| 2,636,864 | 4/1953 | Pye et al. ........................ | 260/662 A |
| 2,783,286 | 2/1957 | Reynolds ........................ | 260/659 A |
| 3,267,160 | 8/1966 | McGreevy et al. .............. | 260/662 A |
| 3,360,483 | 12/1967 | Diamond et al. ............... | 260/662 A |

FOREIGN PATENTS OR APPLICATIONS

| | | | |
|---|---|---|---|
| 1,579,562 | 7/1969 | France ........................... | 260/662 A |

*Primary Examiner*—D. Horwitz

[57] ABSTRACT

A catalyst support composed of silica and magnesia prepared by calcining particles of a silica hydrogel containing magnesium cations and an anion containing chlorine and/or bromine. The supports of this invention can be impregnated with catalytically active components to produce catalysts suitable for use in the non-selective oxychlorination of lower aliphatic hydrocarbons such as ethylene.

17 Claims, No Drawings

PROCESS FOR OXYCHLORINATION OF HYDROCARBONS

This is a division of application Ser. No. 226,929, filed Feb. 16, 1972, now U.S. Pat. No. 3,849,338.

The invention relates to catalyst supports composed of silica and magnesia whose texture properties make them particularly suitable for use in the manufacture of oxychlorination catalysts.

It is widely known that the combination of a rather large number of different properties which are often difficult to combine are sought in catalysts currently in use; this is particularly true for the catalysts intended for fluid or moving bed processes which require careful consideration of the mechanical properties of the catalysts; such mechanical properties sometimes oppose those properties of a strictly catalytic order.

Generally, in methods for the oxychlorination of hydrocarbons, the catalytically active components of the catalysts have been known for a very long time. Copper is usually their principal component, almost always in the form of the chloride, although many additives have been recommended to increase the heat stability of the catalysts, as well as their activity. These additives are extremely diverse and include a large number of metals, such as alkali and earth-alkaline metals, magnesium, beryllium, iron, chrome, cobalt, nickel, manganese, vanadium, tin, bismuth, antimony, uranium, thorium, scandium and the different metals of rare earths. The supports on which these elements are arranged are no less varied; oxides, particularly those of aluminum, silicon and magnesium most frequently enter their formulae. These different oxides are frequently used in a state of natural association or combination, such as pumice stone, clays and bauxites.

However, if perfectly defined special objectives are required in such oxychlorination processes, it is necessary to use a very strict selection among the different possible combinations between the different supports and catalytically active elements. The additional selection of the techniques of fluid or mobile beds further increases the difficulty of providing catalysts as a result of supplementary requirements of resistance, to attrition, for example. When seeking to obtain, by fluid or moving bed processes, a high diversity of chlorinated hydrocarbons during the same oxychlorination operation, referred to as non-selective oxychlorination, it is necessary to reconcile a good overall yield, low combustion of the hydrocarbons and high stability of the catalysts, despite the necessity of operating at relatively elevated temperatures.

For that purpose, there is disclosed a number of catalytic compounds in French Pat. No. 1,579,562, filed on Apr. 24, 1968, where the supports, whose specific surface ranges between 40 and 400 m$^2$/gram, are constituted by spheroid particles formed primarily from silica hydrate and containing at least one other component taken from among compounds of metals of groups IIa, IIIb and IVb, where alumina may be present, and whose catalytically active component is formed of a mixture of copper chloride and at least one chloride taken from the group of alkali or alkaline-earth chlorides with the optional presence of rare earth metal chlorides.

During the course of prolonged industrial tests it became apparent that when catalysts disclosed in various examples of this French patent are used to produce a diversity of the chlorinated products, a low combustion rate and a good overall yield of reaction, other disadvantages of a qualitative order are produced for some of these catalysts, such as the fortuitous appearance of heat-running phenomena and volatilization of catalytically active compounds, sometimes resulting in agglomeration of catalyst granules. Moreover, during the preparation of certain of the catalysts, the textural properties of the supports previously obtained can be unfavorably changed considerably due to inevitable hydrothermal actions, rendering the exact adjustment of the catalytic activity of these catalysts more difficult.

Generally, the catalyst supports composed of silica and magnesia have been known for a very long time and many methods of preparation have been indicated, among them the methods of impregnation of hydrogels of silica by magnesium salt, said impregnation being followed by the precipitation of magnesia by a base like ammonia.

In certain examples of catalysts given by the above-mentioned French patent, the magnesia of the supports used originate from magnesium nitrate and is obtained by simple thermal decomposition of the nitrate after impregnation of the silica hydrogels. However, while these supports are interesting as they are easy to manufacture, they frequently have a tendency to exhibit the above-cited disadvantages.

It is accordingly an object of the present invention to produce and to provide a process for producing a catalyst support formed of silica and magnesia which overcomes the foregoing disadvantages.

It is a more specific object of the invention to produce and to provide a method for producing a catalyst support formed of silica and magnesia for use in oxychlorination catalysts having improved textural characteristics and hydrothermal stability.

It has been found in accordance with the concepts of the present invention that magnesia obtained by thermal decomposition of magnesium compounds in the presence of chlorine and to a lesser degree of bromine-containing anions is capable of conferring special properties on supports which are particularly well-suited for the preparation of oxychlorination catalysts which are non-selective, and which can be used with complete safety in industrial processes of long duration. In addition, the specific surfaces of these supports may also be adjusted easily to values within the suitable interval.

In practice the simplest way to obtain the presence of chlorine and/or bromine anions during the calcination of the supports is to impregnate the silica hydrogel bodies with aqueous solutions of magnesium salts in which the anion is formed from chlorine and/or bromine. However, it may be more interesting in some cases to form these magnesium salts from other magnesium compounds with which these bodies were previously impregnated, or which have been mixed with the silica sols prior to gelification. For example, it is possible to react hydrochloric acid with silica hydrogel bodies impregnated with magnesium acetate or containing magnesium acetate which has been added to the silica sols prior to gelification. It also is possible to add such salts to the silica sols prior to their gelification and particularly when these sols are deionized sols as then no washing problem arises as it is the case when the silica hydrogels are obtained from alkaline silicates. The supports according to the invention may also contain, as secondary components, compounds (oxides, salts, etc.) of the different metals of groups IIa, IIIb and IVb having an atomic weight below 178 as well as aluminum, provided the proportion of magnesia originating from the thermal breakdown of magnesium components in the presence of chlorine and/or bromine anions in the reaction mixture is such that it confers upon the supports the particular properties desired. Supports containing the above secondary components may be desirable to precisely adjust the catalytic activity of the catalysts obtained from these supports.

It appears that in supports prepared in accordance with the concepts of the invention, the nature of the bonds between silica and magnesia is not the same as if the magnesia originated from magnesium nitrate, for example. When magnesia is added to the silica hydrogel bodies according to the invention, its solubility in an ammonium chloride solution appears smaller and the porous volumes of the corresponding supports are in general greater than those of supports obtained otherwise. Moreover, the texture of the original silica hydrogel has little influence on the porous characteristics of the supports obtained, said characteristics depending as a practical matter only on the added proportion of magnesia and the calcination temperature, an advantage from the viewpoint of reproducibility of the results. These particular properties appear to contribute to the good results obtained with non-selective oxychlorination catalysts using such supports, although the reason for this is not completely understood at the present time. In addition, the texture of the supports of the invention remains practically stable during further operations of impregnation by the catalytically active compounds.

In the practice of the method of the invention, the silica hydrogel particles containing magnesium ions and anions containing chlorine or bromine are calcined at an elevated temperature, generally within the range of 530° to 700°C. The amount of magnesium ranges from 10 to 25% by weight based on the weight of the calcined support.

The resulting supports generally have a specific surface area within the range of 70 to 250 m²/g and a porous volume of 0.3 to 1.0 cc/g. Normally greater than 50% of the magnesium content of the support is bound as hereinafter defined.

The resulting support is impregnated with catalytically active components, preferably formed of copper chloride and at least one chloride selected from the group of alkali and alkaline earth metals (e.g. sodium, potassium, calcium, magnesium, etc.) with the optional presence of one or more rare earth metal chlorides, to produce a Deacon type oxyclorination catalyst.

Having described the basic concepts of the invention, reference is now made to the following examples showing comparative reading results effected on supports obtained according to the present invention and on other supports constituted of silica and magnesia and then results obtained by non-selective oxychlorination with catalysts manufactured with certain of these supports having compositions of the type described in the above-cited French patent.

EXAMPLE 1

This example demonstrates the special properties of supports of this invention, wherein the magnesia originates from magnesium chloride, by comparing them to the properties of supports containing the same quantity of magnesia but originating from other magnesium salts, the calcination, operated at the same temperature in all cases, preceded or not by an ammonium precipitation. All samples have been obtained by impregnation of microballs of a silica hydrogel manufactured by coagulation of silica sol drops in a liquid immiscible with water. In dry condition, their diameter on the average is from 40 to 200 microns, their specific surface is 300 m²/g and their porous volume 0.90 cc/gram. These microcalls in hydrogel condition are impregnated with the solutions from various magnesium salts in such quantities and concentrations that the quantity of magnesia obtained in the finished supports is 17% by weight. Then the specific surface S and the porous volume $V_1$ of the supports so obtained are measured, the amount of bonded magnesia expressed in percent of magnesia present and defined as being the magnesia insoluble in an ammonium chloride solution at 200 grams/liter. To show the advantage of the supports according to the invention from the viewpoint of hydrothermal stability, all samples are treated for 2 hours in water at 50°C whereupon the new values $S_2$ and $V_2$ of the specific surface and of the porous volume are measured. Table 1 below summarizes the results obtained:

TABLE 1

| Magnesium salt used | Temperature T Calcination °C | $S_1$ m²/gram | $V_1$ cc/gram | Bound MgO% | $S_2$ m²/gr. | $V_1$ cc/gr. |
|---|---|---|---|---|---|---|
| Chloride (impregnation) | 650 | 76 | 0.75 | 92 | 71 | 0.75 |
| Chloride (impregnation and ammonia precipitation) | 650 | 69 | 0.32 | 90 | 67 | 0.32 |
| Nitrate (impregnation) | 650 | 254 | 0.53 | 32 | 480 | 0.30 |
| Nitrate (impregnation and ammonia precipitation) | 650 | 250 | 0.35 | 32 | 470 | 0.20 |
| Acetate (impregnation) | 650 | 235 | 0.70 | 7.6 | 655 | 0.50 |
| Acetate (impregnation and ammonia precipitation) | 650 | 290 | 0.41 | 11 | 645 | 0.53 |

This example clearly indicates the profound differences between the supports where the magnesia is obtained from magnesium chloride and the others, as the supports of the invention have good stability to the hydrothermal treatments as shown by the low buildup of their specific surface and their porous volume. Only the supports of this invention possess a high proportion of bound magnesium.

EXAMPLE 2

Using the same general procedure as described in Example 1, silica hydrogel microballs of the same dimensions but having a 600 m²/gram specific surface and 0.6 cc/gram porous volume, are treated with a magnesium chloride or magnesium nitrate solution so that a proportion of 15% by weight of magnesium is obtained in the finished support, after simple calcination. The calcination temperatures are 600° and 650°C for chloride and 650° and 720°C for nitrate.
The results are compiled in Table 2 below:

TABLE 2

| Magnesium Salt Used | Temperature T Calcination °C | $S_1$ m²/gr. | $V_1$ cc/g | Bound MgO% | $S_2$ m²/g | $V_2$ cc/g |
|---|---|---|---|---|---|---|
| Chloride | 600 | 120 | 0.73 | 76 | 125 | 0.73 |
|  | 650 | 77 | 0.75 | 90 | 80 | 0.73 |
| Nitrate | 650 | 310 | 0.36 | 40 | 450 | 0.28 |
|  | 720 | 80 | 0.25 | 70 | 110 | 0.22 |

By comparison with the preceding example this example shows that by simple variation of the temperature of calcination, it is possible to obtain from magnesium chloride notably different specific surfaces, the porous volumes remaining constant and a sufficient proportion of bound magnesium, while obtaining surfaces of the same order as supports prepared from magnesium nitrate calcined at 720°C. Such a high calcination temperature in the case of the support prepared from the nitrate causes a considerable reduction of the porous volume; the proportion of bound magnesia although large, does not attain that of the support obtained with magnesia originating from magnesium chloride.

EXAMPLE 3

This example relates to the manufacture of supports where the magnesia is obtained by calcination of magnesium chloride formed inside the hydrogel bodies from a magnesium compound introduced there first.

The same microballs as those in Example 1 are impregnated with a quantity of magnesium acetate corresponding to 17% by weight of magnesia in relation to the finished support. These balls are then treated with hydrochloric acid in dilute solution to from therein magnesium chloride; the values found for the same sizes as those of preceding examples and for calcination temperatures of 650° and 700°C are compiled in Table 3 below:

TABLE 3

| Magnesium Salt Used | Temperature T Calcination °C | $S_1$ m²/g | $V_1$ cc/g | Bound m²/g | $S_2$ cc/g | $V_2$ |
|---|---|---|---|---|---|---|
| Acetate, then HCl treatment | 650 | 110 | 0.65 | 57 | 150 | 0.64 |
|  | 700 | 82 | 0.60 | 74 | 90 | 0.56 |

The general results are the same as those shown in the preceding examples but the temperatures of calcination necessary appear to have to be higher. The quantity of bound magnesia is sufficient and the preservation of the texture continues despite the hydrothermal treatment.

EXAMPLE 4

This example relates to supports with different magnesia contents originating from magnesium chloride and it is intended to show that the proportion of magnesia bound is always strong an substantially independent of the contents of these magnesia supports. The supports are prepared with the same microballs of silica as those used in Example 1, by impregnation with solutions of different contents of magnesium chloride according to the content of magnesia to be obtained. The decomposition is made by calcination at 600° and 660°C. The results obtained are compiled in Table 4 below:

TABLE 4

| Proportion of MgO in the support % by weight | Temperature T Calcination °C | $S_1$ m²/g. | $V_1$ cc/g. | MgO bound % | $S_2$ m²/g. | $V_2$ cc/g. |
|---|---|---|---|---|---|---|
| 10 | 600 | 238 | 0.70 | 74 | 241 | 0.69 |
|  | 660 | 78 | 0.66 | 77 | 90 | 0.65 |
| 17 | 600 | 104 | 0.78 | 79 | 95 | 0.78 |
|  | 660 | 76 | 0.75 | 92 | 71 | 0.75 |
| 25 | 600 | 61 | 0.47 | 69 | 70 | 0.44 |
|  | 660 | 52 | 0.47 | 72 | 56 | 0.43 |

EXAMPLE 5

This example relates to the preparation of supports in which the magnesia is obtained by thermal decomposition at different temperatures of magnesium perchlorate after impregnation of the same silica supports as the ones used in Example 1; the proportion of this magnesia is 17% by weight of the finished support. Table 5 below shows the results obtained:

TABLE 5

| Magnesium Salt Used | Temperature T Calcination °C | $S_1$ m²/g. | $V_1$ cc/g. | bound MgO% | $S_2$ m²/g. | $V_2$ cc/g. |
|---|---|---|---|---|---|---|
| PERCHLORATE (impregnation) | 600 | 177 | 0.68 | 62 | 293 | 0.63 |
|  | 650 | 110 | 0.54 | 84 | 108 | 0.54 |
|  | 700 | 18 | 0.36 | 93 | 24 | 0.38 |

This example shows that the action of the chlorine of magnesium perchlorate is analogous to that of the Cl⁻ ion because the stability of the hydrothermal type of the products obtained is good and the proportion of bound magnesium is high.

EXAMPLE 6

This example relates to the application of two supports selected from those of Example 2. Both these supports, whose magnesia is obtained from magnesium chloride are impregnated with a cuprous chloride and potassium chloride solution in such a manner that both finished catalysts have metal chloride contents expressed in % by weight of the metals of 3.5% and 1.3%, respectively. The experiments in the oxychlorination of ethylene of these two catalysts are conducted in a fluid bed reactor whose temperature is maintained at 340°C, constituted by a vertical glass tube whose inner diameter is 2 cm. The height of the catalyst to be tested placed therein, measured at rest, is 7.5 cm. The fluidization of the catalyst is obtained by a gaseous jet of a mixture of ethylene, hydrogen chloride gas and air, the ethylene yield being established at a flow rate of 8 liters/hour, measured at normal pressure and temperature, the ratio in $HCl/C_2H_4$ molecules being equal to 2.25 and the ratio in $O_2/C_2H_4$ molecules being equal to 0.70. The approximate contact time is 1 second. At the discharge from the reactor the gas jet, analyzed by chromatography, is constituted by a small amount of unconverted ethylene, by a small amount of $CO_2$ and a mixture of chlorinated hydrocarbons comprising in their major part 1,2-dichloroethane, and smaller quantities of 1,1,2-trichloroethane and symmetric tetrachloroethane.

For both these examples the results obtained for the following ratios are shown in Table 6 below:

Overall conversion rate of ethylene, $X_g$.

Conversion rate of ethylene to $CO_2$, $X_{CO}$.

$Se_1$ selectivity, conversion rate of ethylene to 1,2-dichloroethane based on the overall conversion rate of ethylene.

$Se_2$ selectivity, conversion rate of ethylene to 1,1,2-trichloroethane based on the overall conversion rate of ethylene.

$Se_3$ selectivity, conversion rate of ethylene to symmetrical tetrachloroethane based on the overall conversion rate of ethylene.

Ratio $\phi$ of the sum of the quantities produced of 1,1,2-trichloroethane and symmetrical tetrachloroethane to the sum of the quantities produced of 1,2-dichloroethane, 1,1,2-trichloroethane and symmetric tetrachloroethane, expressed in mole ratios. This ratio thus indicates the ability of the catalyst to produce a mixture of the chlorinated hydrocarbons cited, that is, the degree of non-selectivity.

TABLE 6

| Temperature T calcination of the support°C | $X_g$ | $XCO_2$ | $Se_1$ | $Se_2$ | $Se_3$ | $\phi$ |
|---|---|---|---|---|---|---|
| 600 | 88 | 0.2 | 84 | 9 | 5 | 14 |
| 650 | 75 | 0.1 | 89 | 7 | 3 | 10 |

Both these catalysts are suitable for non-selective industrial oxychlorination operations, said non-selectivity being demonstrated by the $\phi$ ratios obtained; the combustion rates are low and the activities sufficient. During these operations these catalysts age only slightly. It is noted that the granules do not stick to each other due to the volatilization of the catalytically active compounds. Moreover, the resistance to attrition is good due to the use of supports obtained from microballs of silica gel. Finally, during these industrial oxychlorination operations no incident of heat balling was noted, contrary to what may sometimes occur with the use of analogous catalysts wherein the magnesia is obtained by calcination of magnesium nitrate.

We claim:

1. In the process for the oxyclorination of hydrocarbons wherein a mixture of a lower aliphatic hydrocarbon, hydrogen chloride and a molecular oxygen-containing gas are reacted to produce chlorinated hydrocarbons, the improvement comprising carrying out the reaction in the presence of a catalyst consisting essentially of copper chloride deposited on a support of silica and magnesia prepared by calcining at a temperature within the range of 530° to 700°C bodies of a silica hydrogel containing a compound selected from the group consisting of magnesium chloride, magnesium bromide, magnesium perchlorate and mixtures thereof, with the hydrogel containing 10 to 25% by weight of magnesia based on the calcined particles.

2. A process as defined in claim 1 wherein the hydrogel contains magnesium chloride or bromide.

3. A process as defined in claim 1 wherein the hydrogel contains magnesium perchlorate.

4. A process as defined in claim 1 wherein the hydrogel particles contain the magnesium salt of an organic carboxylic acid, and are reacted with hydrogen chloride prior to calcination.

5. A process as defined in claim 1 wherein the hydrogel particles are spheroid.

6. A process as defined in claim 1 wherein at least 50% of the magnesia present is bound, based on the proportion of magnesia present which is insoluble in a solution of 200 g/l of ammonium chloride.

7. A process as defined in claim 1 wherein the catalyst includes at least one oxide of a metal selected from the group consisting of the metals of groups II($a$), III($b$) and IV($b$) having an atomic weight below 178 and at least one rare earth metal chloride.

8. A process as defined in claim 1 wherein the support has a surface area within the range of 70 to 250 m²/gram.

9. A process as defined in claim 1 wherein the support has a porous volume of 0.3 to 1 cc/g.

10. A process as defined in claim 1 wherein the catalyst includes at least one chloride of a metal selected from the group consisting of alkali and alkaline earth metals.

11. A process as defined in claim 1 wherein the catalyst includes at least one rare earth metal chloride.

12. A process as defined in claim 1 wherein the lower aliphatic hydrocarbon is ethylene.

13. A process for the production of 1,2-dichloroethane, 1,1,2-trichloroethane and 1,1,2,2-tetrachloroethane by oxychlorination of ethylene comprising the steps of contacting ethylene, hydrogen chloride and a molecular oxygen containing gas in the presence of a catalyst consisting essentially of copper chloride deposited on a support of silica and magnesia prepared by calcining at a temperature within the range of 530° to 700°C bodies of a silica hydrogel containing a compound selected from the group consisting of magnesium chloride, magnesium bromide, magnesium perchlorate and mixtures thereof, with the hydrogel containing 10 to 25% by weight of magnesia based on the calcined particles.

14. A process as defined in claim 13 wherein the catalyst also contains at least one chloride of a metal selected from the group consisting of an alkali metal and an alkaline earth metal.

15. A process as defined in claim 13 wherein the catalyst includes at least one rare earth metal chloride.

16. A process as defined in claim 13 wherein the support also contains at least one oxide of a metal selected from the group consisting of group II, IIIB and IVB having an atomic weight below 178.

17. In the process for the oxychlorination of hydrocarbons wherein a mixture of a lower aliphatic hydrocarbon, hydrogen chloride and a molecular oxygen-containing gas are reacted to produce chlorinated hydrocarbons, the improvement comprising carrying out the reaction in the presence of a catalyst consisting essentially of copper chloride deposited on a support of silica and magnesia prepared by calcining at a temperature within a range of 530° to 700°C spherical bodies of silica hydrogel impregnated with a compound selected from the group consisting of magnesium chloride, magnesium bromide, magnesium perchlorate and mixtures thereof, with the hydrogel containing 10 to 25% by weight of magnesia based on the calcined particles.

* * * * *

UNITED STATES PATENT OFFICE
CERTIFICATE OF CORRECTION

Patent No. 3,969,424     Dated July 13, 1976
S.N. 502,804

Inventor(s) Jean-Claude DAUMAS and Madeleine Le Page

It is certified that error appears in the above-identified patent and that said Letters Patent are hereby corrected as shown below:

IN THE SPECIFICATION:

In column 5, Table 3, the titles in the last three columns should read:

Bound MgO%     $S_2$ $m^2/g$     $V_2$ $cc/g$

Signed and Sealed this

Nineteenth Day of October 1976

[SEAL]

Attest:

RUTH C. MASON
*Attesting Officer*

C. MARSHALL DANN
*Commissioner of Patents and Trademarks*